United States Patent [19]

MacMillan

[11] 4,228,159
[45] Oct. 14, 1980

[54] STABILIZATION OF VITAMIN A IN PRESENCE OF TRACE MINERALS

[75] Inventor: Melvin J. MacMillan, Cranford, N.J.

[73] Assignee: Diamond Shamrock Corporation, Dallas, Tex.

[21] Appl. No.: 49,097

[22] Filed: Jun. 18, 1979

[51] Int. Cl.$^3$ ............ A61K 31/00; A61K 47/00; A61K 31/07; A61K 33/24

[52] U.S. Cl. .................. 424/175; 424/131; 424/142; 424/144; 424/145; 424/147; 424/150; 424/153; 424/344

[58] Field of Search ............ 424/344, 175, 131, 142, 424/144, 145, 147, 150, 153

[56] References Cited

U.S. PATENT DOCUMENTS

| | | | |
|---|---|---|---|
| 2,827,452 | 3/1958 | Schlenk et al. | 424/344 |
| 2,897,119 | 7/1959 | Dunn | 424/344 |
| 2,973,266 | 2/1961 | Rosenberg | 424/344 |

FOREIGN PATENT DOCUMENTS

| | | | |
|---|---|---|---|
| 205711 | 1/1955 | Australia | 424/344 |
| 553210 | 2/1958 | Canada | |
| 1263222 | 11/1958 | France | 424/344 |

OTHER PUBLICATIONS

Georgia–Pacific–Technical Bulletins to Perma–Pel and Lignosite–G. P. Lig, 5/70–R.

*Primary Examiner*—Douglas W. Robinson
*Attorney, Agent, or Firm*—Neal T. Levin

[57] ABSTRACT

Trace minerals when in contact with vitamin A in animal feed supplements and in animal feed have a deleterious effect upon vitamin A. This effect is reduced by treating trace minerals with lignin sulfonates before bringing the trace minerals into contact with vitamin A.

16 Claims, No Drawings

STABILIZATION OF VITAMIN A IN PRESENCE OF TRACE MINERALS

BACKGROUND OF THE INVENTION

1. Field of the Invention

This invention relates to trace mineral supplements which are suitable for addition to vitamin A-containing supplements.

2. Description of the Prior Art

It is common practice to add various minerals to poultry and livestock feeds. For example, many such feeds have mineral supplements added to them which are mixtures of materials such as limestone, steamed bone meal, dicalcium phosphate and salt. Such mineral materials are added to poultry and livestock feeds in amounts which are comparatively large as compared to the amounts of so-called trace minerals which are added to such feeds. The trace minerals most frequently added to feeds are compounds of manganese, copper, iron, cobalt, iodine, zinc and selenium. Supplementary amounts of these trace minerals are usually considered necessary for ruminants and all of them, with the exception of cobalt, are considered necessary additions for swine and poultry feeds.

It is also common practice to supplement poultry and livestock feeds with vitamin A. In many cases feed manufacturers purchase supplements for addition to their feeds which contain both vitamin A and minerals, including trace minerals. These supplements are quite often referred to as premixes, although they may contain other ingredients such as limestone and antibiotics.

Most minerals, particularly trace minerals, have a very detrimental effect on vitamin A. This is especially so in vitamin and mineral supplements because the concentration of minerals is considerably higher than in the finished feed product. The problem is intensified where the supplement or feed which contains both the vitamin and trace minerals is exposed to large amounts of moisture. Degradation of the vitamin also varies depending upon the nature of the carrier for the vitamin. Attempts have been made in the past to provide trace minerals in a form in which they will not detrimentally affect the stability of the vitamin. For example, according to Canadian Pat. No. 553,210—Hochberg—Feb. 11, 1958, trace mineral supplements have been prepared by admixing trace minerals with a normally solid wax-like material and a vegetable meal.

SUMMARY OF THE INVENTION

Trace mineral supplements containing one or more trace minerals can be prepared which when admixed with vitamin A have a less detrimental effect upon vitamin A. This is accomplished by adding lignin sulfonates to trace minerals before the latter are brought into contact with vitamin A. From about 2% to about 25% by weight of lignin sulfonates, calculated on a dry basis, based on the total weight of the trace minerals and lignin sulfonate is admixed with the trace minerals which are usually in the form of finely divided powders. Unless a solution of lignin sulfonates is used, moisture is added to the mixture of trace minerals and lignin sulfonates in an amount sufficient to solubilize the lignin sulfonates so that the latter can coat the trace minerals. Usually, no more moisture is added than is needed to form a slurry of the trace minerals and lignin sulfonates. Moisture can be added by spraying, by exposure to live steam or by adding water directly to the mixture. After proper wetting and blending, the mass is then dried by means such as a vacuum oven, spray drier, heated rolls, extruder or similar equipment suitable for the removal of the applied moisture. After drying, the product may be sized to a suitable fraction which is compatible with feeds or premixes.

DESCRIPTION OF THE PREFERRED EMBODIMENTS

Regarding selection of trace minerals any trace mineral which it is desired to incorporate in the finished animal or poultry feed may be used, the most common being manganese, copper, iron, cobalt, iodine, zinc and their mixtures. These trace minerals are usually in the form of their oxides, carbonates or their salts such as sulfates. Examples are copper oxide, copper sulfate, iron sulfate, cobalt carbonate, potassium iodide and copper iodide. These trace minerals are usually in the form of fine powders, i.e., finer than 100 mesh screen (U.S. Standard Series).

Lignin sulfonates are well-known materials. They are prepared from the waste liquors of sulfite pulping. Preferred are the water-soluble ammonium, sodium, calcium and magnesium lignin sulfonates. These products are available as aqueous concentrates or as spray or drum dried powders. When exposed to the digestive fluids of the animal, the lignin sulfonates separate from the trace minerals. Preferably, dry powdered lignin sulfonates are used with a minimum amount of moisture when mixing with the trace minerals. Preferably, 10% by weight of dry, solid lignin sulfonates is used, based upon the weight of trace minerals and lignin sulfonates. Final particle size of the treated trace minerals preferably is such that the majority of the particles pass through a 16 mesh screen (U.S. Standard Series) but essentially all will be retained on an 80 mesh screen (U.S. Standard Series), preferably on a 60 mesh screen (U.S. Standard Series) so that a multiplicity of small, solid granular particles is obtained. Note that hereinafter all screen sizes are understood to be based on the U.S. Standard Series of screens.

The vitamin A is usually in a matrix such as starch or in an oil carrier such as vegetable oil, e.g., cotton seed oil, corn oil, etc. Vitamin A is usually used as vitamin A acetate or vitamin A palmitate.

For a fuller understanding of this invention, reference may be made to the following examples. These examples are given merely to illustrate the invention and are not to be construed in a limiting sense.

EXAMPLE I

A trace mineral mix having the following composition was prepared:

| Trace Minerals | % by Weight of Compound | % by Weight of Element |
|---|---|---|
| Manganous oxide | 84.75 | 55.0 Mn |
| Copper sulfate | 6.60 | 1.65 Cu |
| Cuprous iodide | 1.70 | 1.11 I, 0.55 Cu |
| Cobalt Carbonate | 0.25 | 0.115 Co |
| Calcium Carbonate | 6–7 | 2–3 Ca |

This trace mineral mix is used in feed for poultry, ruminants and swine. Dry powdered lignin sulfonates identified as Stapel and having the following composition was obtained from Consolidated Papers, Inc. (Appleton Wisconsin):

|  | % by Weight (Approx.) |
|---|---|
| Calcium lignin sulfonates | 52 |
| Reducing sugars |  |
| Hexoses | 17 |
| Pentoses | 8 |
| More complex sugars | 19 |
| Moisture | 5 |
| Inorganics | 4 |

Portions of the above trace mineral mix and dry powdered lignin sulfonates were admixed in a weight ratio of 90% by weight trace minerals and 10% by weight lignin sulfonates. Then water was added to the mixture in an amount to wet the mixture sufficiently until it appeared damp or crumbly wet. Blending was carried out for a sufficient time to allow wetting of the mixture. Thereafter, the moisture was removed by placing the mixture in a vacuum oven. Finally, the mixture was sized to a particle size such that all particles passed through a 20 mesh screen and were retained on a 40 mesh screen.

Portions of the above trace mineral mixture, both treated with lignin sulfonates and untreated, were fortified to 1000 USP units of vitamin A per gram with vitamin A palmitate. The vitamin A palmitate was in a starch matrix and in the form of small platelets. The vitamin A particle size was such that all particles passed through a 20 mesh screen and essentially all were retained on a 60 mesh screen. Also, for comparison purposes, the same vitamin A palmitate in a starch matrix having a potency of 325,000 USP units per gram was included in the stability study. Approximately 0.3 gram portions of the vitamin A and approximately ten gram portions of the treated and untreated trace mineral mixtures fortified with vitamin A were assayed for vitamin A activity. The assays were performed using the United States Pharmacopeia Method, 19th Edition (1975) with slight modification because of the presence of the starch matrix, i.e., isopropanol was substituted for ethanol in the saponification step. The remaining materials were placed in capped glass containers and stored in a convection oven at 45° C. At intervals of three, six, nine, and twelve weeks, samples were removed and assayed for vitamin A activity using the previously described sample quantities and assay method. The results appear in Table I.

TABLE I

| Time (Wks.) @ 45° C. | Vitamin A (USP Units/gm) | Vitamin A Activity of Mixture of Vitamin A and Untreated Trace Minerals (Control) (USP Units/gm) | Vitamin A Activity of Mixture of Vitamin A and Trace Minerals Treated with Lignin Sulfonates (USP Units/gm) |
|---|---|---|---|
| Initial | 330,000 (100.0%) | 1,030 (100.0%) | 1,083 (100.0%) |
| 3 | 309,000 (93.6%) | 851 (82.6%) | 1,310 (120.0%) |
| 6 | 279,000 (84.4%) | 772 (75.0%) | 1,150 (106.2%) |
| 9 | 274,000 (83.0%) | — | 1,110 (102.5%) |
| 12 | 246,000 (74.5%) | 685 (66.5%) | 1,150 (106.2%) |

In the above table, the percentages represent percent vitamin A activity based on initial activity. All data reported in this table are within experimental error.

EXAMPLE II

This example illustrates use of lignin sulfonates in a more dilute trace mineral mix. Trace mineral mix and calcium lignin sulfonates having the same composition as disclosed in Example I were used in this example. In the same manner as carried out in Example I, a trace mineral mix treated with calcium lignin sulfonates was prepared having a weight ratio of 90% by weight trace minerals and 10% by weight calcium lignin sulfonates.

Portions of the above trace mineral mix both treated with lignin sulfonates and untreated were mixed with ground limestone (calcium carbonate). The untreated product was made by mixing 16% by weight trace mineral mix with 84% by weight ground limestone. The treated product was made by mixing 17.8% by weight coated trace mineral mix (16% ÷ 0.90) with 82.2% by weight ground limestone. The particle size of the limestone was such that all particles passed through a 20 mesh screen and not more than 30% by weight passed through a 100 mesh screen.

Portions of the above limestone-trace mineral mix, both treated with lignin sulfonates and untreated were fortified to 1000 USP units of vitamin A per gram with vitamin A palmitate. The vitamin A palmitate was the same as used in Example I. Approximately ten gram portions of the treated and untreated trace mineral mixtures diluted with limestone and fortified with vitamin A were assayed for vitamin A activity as described in Example I. The remaining materials were placed in capped glass containers and stored in a convection oven at 45° C. At intervals of three, six and twelve weeks, samples were removed and assayed for vitamin A activity using the previously described sample quantities and assay method. The results appear in Table II.

TABLE II

| Time (Wks.) @ 45° C. | Vitamin A Activity of Mixture of Vitamin A and Untreated Trace Minerals (Control) diluted with Limestone (USP Units/gm) | | | Vitamin A Activity of Mixture of Vitamin A and Trace Minerals Treated with Lignin Sulfonates diluted with Limestone (USP Units/gm) | | |
|---|---|---|---|---|---|---|
| Initial | 870 903 | 886.5 | 100.0% | 933 939 | 936.0 | 100.0% |
| 3 | 780 704 | 742.0 | 83.7% | 732 720 | 726.0 | 77.6% |
| 6 | 679 — | 679.0 | 76.6% | 754 697 | 725.5 | 77.5% |
| 12 | 681 507 | 562.5 | 63.4% | 738 659 | 698.5 | 74.6% |

In the above table, the percentages represent percent vitamin A activity based on initial activity. All data reported in this table are within experimental error.

EXAMPLE III

A trace mineral mix having the following composition was prepared.

| Trace Mineral | % by Weight of Compound | % by Weight of Element |
|---|---|---|
| Zinc oxide (70% Zn) | 28.32 | 19.8 Zn |
| Maganous oxide (65% Mn) | 12.30 | 8.0 Mn |
| Ferrous sulfate (32% Fe) | 46.88 | 15.0 Fe |
| Copper Sulfate (25% Cu) | 12.00 | 3.0 Cu |
| Cuprous iodide (32.6% Cu, 65.2% I) | 0.46 | 0.3 I, 0.15 Cu |
| Sodium selenite (45.65% Se) | 0.044 | 0.02 Se |

In the same manner as described in Example I, portions of the above trace mineral mix were mixed with calcium lignin sulfonates having the same composition as disclosed in Example I in the following weight ratios.

| Ingredients | % by Weight | | | | |
|---|---|---|---|---|---|
| Trace Mineral Mix | 100 | 97.5 | 95 | 90 | 85 |

| Ingredients | % by Weight | | | | |
|---|---|---|---|---|---|
| Calcium lignin sulfonates | 0 | 2.5 | 5 | 10 | 15 |

Each portion was then mixed with ground limestone so that each product contained a constant amount (50% by weight) of trace minerals. The amount of limestone in each product was adjusted to compensate for the various levels of lignin sulfonate added. For example the untreated product contained 50% by weight trace mineral mix plus 50% by weight limestone while the last product contained 58.8% by weight coated trace minerals (50% trace minerals÷0.85) and 41.2% by weight limestone. Each portion was then fortified to 1000 USP units of vitamin A per gram with vitamin A palmitate. The vitamin A palmitate was the same as used in Example I and the limestone was the same as used in Example II. Approximately ten gram portions of each of the five different compositions were assayed for vitamin A activity as described in Example I. The remaining quantities were placed in capped glass containers and stored in a convection oven at 45° C. At intervals of three, six and twelve weeks, samples were removed and assayed for vitamin A activity using the previously described sample quantities and assay method. The results appear in Table IV. All data are the average of duplicate determinations.

stone as described in Example II in a weight ratio of 17.8% by weight of trace mineral mix and 82.2% by weight of limestone. The limestone-trace mineral mix was fortified to 1000 USP units of vitamin A per gram with vitamin A palmitate. The vitamin A palmitate was the same as used in Example I. Approximately ten gram portions of the treated trace mineral mixture diluted with limestone and fortified with vitamin A were assayed for vitamin A activity as described in Example I. The remaining materials were placed in capped glass containers and stored in a convection oven at 45° C. At intervals of three, six and twelve weeks, samples were removed and assayed for vitamin A activity using the previously described sample quantities and assay method. The results appear in Table IV. For purposes of comparison with an untreated trace mineral mix diluted with limestone, reference is made to the data set forth in Table II, Columns 2, 3 and 4, which data are repeated in Table IV.

TABLE IV

| Time (Wks.) @ 45° C. | Vitamin A Activity of Mixture of Vitamin A and Untreated Trace Minerals (Control) diluted with Limestone (USP Units/gm) | | | Vitamin A Activity of Mixture of Vitamin A and Trace Minerals Treated with Lignin Sulfonates diluted with Limestone (USP Units/gm) | | |
|---|---|---|---|---|---|---|
| Initial | 870 903 | 886.5 | 100.0% | 883 855 | 869.0 | 100.0% |
| 3 | 780 | 742.0 | 83.7% | 825 | 803.0 | 92.4% |
| 6 | 704 679 | 679.0 | 76.6% | 781 826 640 | 733.0 | 84.3% |
| 12 | 618 507 | 562.5 | 63.4% | 681 718 | 699.5 | 80.5% |

In the above table, the percentages represent percent vitamin A activity based on initial activity. All data reported in this table are within experimental error.

TABLE III

| Time (Wks.) @ 45° C. | | Vitamin A Activity of Mixtures of Vitamin A and Untreated and Treated Trace Minerals Diluted with Calcium Carbonate (USP Units/gm) | | | | | | | | |
|---|---|---|---|---|---|---|---|---|---|---|
| | % Trace Mineral Mix | 100 | | 97.5 | | 95 | | 90 | | 85 |
| | % Calcium Lignin Sulfonates | 0 | | 2.5 | | 5 | | 10 | | 15 |
| Initial | | 889.5 | (100.0%) | 881.5 | (100.0%) | 930.5 | (100.0%) | 858.0 | (100.0%) | 1,004.0 (100.0%) |
| 3 | | 722.5 | (81.2%) | 816.5 | (92.6%) | 814.0 | (87.5%) | 814.0 | (94.9%) | 844.0 (84.1%) |
| 6 | | 700.0 | (78.7%) | 763.0 | (86.6%) | 736.5 | (79.2%) | 742.0 | (86.5%) | 692.0 (68.9%) |
| 12 | | 571.0 | (64.2%) | 696.0 | (79.0%) | 688.0 | (73.9%) | 663.0 | (77.3%) | 722.5 (72.0%) |

In the above table, the percentages represent percent Vitamin A activity based on initial activity. All data reported in this table are within experimental error.

EXAMPLE IV

In the same manner as carried out in Example I, a trace mineral mix as described in Example I, treated with ammonium lignin sulfonates obtained from Finch, Pruyn & Company (Glens Falls, New York) and used as is, was prepared having a weight ratio of 90% by weight trace minerals and 10% by weight ammonium lignin sulfonates. Sufficient lignin sulfonate product was used to give 10% by weight of lignin sulfonates. The lignin sulfonate had the following composition:

| | % by Weight |
|---|---|
| Ammonium lignin sulfonate | 45.10 |
| Wood sugars | 12.90 |
| Hemicelluloses and other carbohydrates | 41.28 |
| Ash | 0.72 |
| Appearance | Dark Liquid |
| pH | 5.17 |
| Solids | 49.96 |
| Viscosity | 60 centipoise @ 20° C. |
| Nitrogen | 8.04 |
| Specific gravity | 1.2251 @ 20° C. |
| Total Sulfur | 11.49 |
| Flash Point | Will not flash below boiling point of water |
| Solubility | Completely soluble in water |

After slurrying and drying in a vacuum oven, the treated trace mineral mix was mixed with ground lime- While the invention has been described with reference to certain specific embodiments thereof, it is understood that it is not to be so limited since alterations and changes may be made therein which are within the full intended scope of the appended claims.

What is claimed is:

1. An admixture of vitamin A and a trace mineral supplement containing at least one trace mineral wherein said supplement is composed of small, solid granular particles, the majority of said particles being of a size such that they pass through a 16 mesh screen, but essentially all are retained on an 80 mesh screen, each particle being an intimate mixture of:
   (a) at least one trace mineral coated with
   (b) an effective amount of lignin sulfonates to reduce degradation of vitamin A when in contact with said trace mineral.

2. The vitamin, trace mineral admixture of claim 1 wherein the particle size of said trace mineral supplement is such that the majority of said particles pass through a 16 mesh screen, but essentially all are retained on a 60 mesh screen.

3. The vitamin, trace mineral admixture of claim 1 wherein there is present in said supplement from about 2% by weight to about 25% by weight of lignin sulfonates and from about 98% by weight to about 75% by weight of at least one trace mineral.

4. The vitamin, trace mineral admixture of claim 3 wherein there is present in said supplement about 90% by weight of trace mineral and about 10% by weight of lignin sulfonates.

5. The vitamin, trace mineral admixture of claim 3 wherein said trace mineral is at least one selected from the group consisting of manganese, copper, iron, cobalt, iodine, zinc, selenium and magnesium.

6. The vitamin, trace mineral admixture of claim 3 wherein said vitamin A is present in a starch matrix.

7. The vitamin, trace mineral admixture of claim 6 wherein said vitamin A is vitamin A palmitate.

8. The vitamin, trace mineral mixture of claim 3 wherein said lignin sulfonates are calcimum lignin sulfonates.

9. The vitamin, trace mineral admixture of claim 3 wherein said lignin sulfonates are ammonium lignin sulfonates.

10. A process of stabilizing vitamin A in the presence of a trace mineral supplement containing at least one trace mineral comprising admixing vitamin A with said supplement which is composed of small, solid granular particles, the majority of said particles being of a size such that they pass through a 16 mesh screen, but essentially all are retained on an 80 mesh screen, each particle being an intimate mixture of:
   (a) at least one trace mineral coated with
   (b) an effective amount of lignin sulfonates to reduce degradation of vitamin A when in contact with said trace mineral.

11. The process of claim 10 wherein the particle size of said supplement is such that the majority of said particles pass through a 16 mesh screen, but essentially all are retained on a 60 mesh screen.

12. The process of claim 10 wherein there is present in said supplement from about 2% by weight to about 25% by weight of lignin sulfonates and from about 98% by weight to about 75% by weight of at least one trace mineral.

13. The process of claim 12 wherein there is present in said supplement about 90% by weight of trace mineral and about 10% by weight of lignin sulfonates.

14. The process of claim 12 wherein said lignin sulfonates are calcium lignin sulfonates.

15. The process of claim 12 wherein said lignin sulfonates are ammonium lignin sulfonates.

16. The process of claim 12 wherein said trace mineral is at least one selected from the group consisting of manganese, copper, iron, cobalt, iodine, zinc, selenium and magnesium.

* * * * *